(12) United States Patent
Manzer et al.

(10) Patent No.: US 6,624,337 B1
(45) Date of Patent: Sep. 23, 2003

(54) PROCESS FOR THE MANUFACTURE OF FLUOROOLEFINS

(75) Inventors: Leo E. Manzer, Wilmington, DE (US); Cynthia A. Lundgren, Rising Sun, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/979,784

(22) PCT Filed: Jun. 2, 2000

(86) PCT No.: PCT/US00/15318
§ 371 (c)(1),
(2), (4) Date: Nov. 21, 2001

(87) PCT Pub. No.: WO00/75092
PCT Pub. Date: Dec. 14, 2000

Related U.S. Application Data

(60) Provisional application No. 60/137,460, filed on Jun. 4, 1999.

(51) Int. Cl.⁷ .................................. C07C 21/18
(52) U.S. Cl. ........................................ 570/153
(58) Field of Search .......................... 570/153

(56) References Cited

U.S. PATENT DOCUMENTS

| 2,404,374 A | 7/1946 | Harmon |
| 2,462,345 A | 2/1949 | Barrick |
| 2,519,983 A | 8/1950 | Simons |
| 2,713,593 A | 7/1955 | Brice et al. |
| 3,511,760 A | 5/1970 | Fox et al. |
| 3,662,009 A | * 5/1972 | Hutchinson |
| 3,789,088 A | 1/1974 | Lalande, Jr. et al. |
| 4,086,407 A | 4/1978 | Fozzard |
| 4,978,649 A | 12/1990 | Surovikin et al. |

FOREIGN PATENT DOCUMENTS

| EP | 0 455 399 A2 | 11/1991 |
| EP | 0 455 399 A3 | 11/1991 |
| WO | WO 95/21126 | 8/1995 |

* cited by examiner

*Primary Examiner*—Michael L. Shippen

(57) ABSTRACT

A process is disclosed for producing perfluoroolefins of the formula $CF(R^1_f)=CF_2$, where $R^1_f$ is F or $CF_3$. The process involves (a) perfluorinating cyclobutanes of the formula

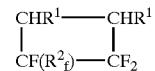

where $R^2_f$ is F or $CF_3$, and where one $R^1$ is H and the other $R^1$ is H when $R^1_f$ is F and is $CH_3$ when $R^1_f$ is $CF_3$, by the Simons electrochemical fluorination process in an electrochemical cell in a solution of anhydrous liquid hydrogen fluoride under temperature and pressure conditions sufficient to replace all hydrogens in the cyclobutane of the above formula with fluorine; and (b) cracking the perfluorinated cyclobutane. A disclosed cracking involves contacting the perfluorinated cyclobutanes with carbon or a conductive metal, which is heated by induction heating to a temperature sufficient to crack the perfluorinated cyclobutanes.

16 Claims, No Drawings

PROCESS FOR THE MANUFACTURE OF FLUOROOLEFINS

This application represents a national filing under 35 USC 371 of International Application No. PCT/US00/15318 filed Jun. 2, 2000 and claims the priority benefit of U.S. Provisional Application No. 60/137,460 filed Jun. 4, 1999.

FIELD OF THE INVENTION

This invention relates to a process for the production of perfluoroolefins by the thermal cracking of perfluorinated cyclobutanes prepared by Simons electrofluorination. More particularly perfluorocyclobutane is converted to tetrafluoroethylene and perfluoromethylperfluorocyclobutane is converted to a mixture of tetrafluoroethylene and hexafluoropropylene.

BACKGROUND

Tetrafluoroethylene (i.e., $CF_2=CF_2$ or TFE) and hexafluoropropylene (i.e., $CF_3CF=CF_2$ or HFP) are monomers used for the preparation of a variety of fluoropolymers. Typical fluoropolymer properties which enhance their utility include: excellent electrical insulation, resistance to attack by chemicals, wide service temperatures, from near absolute zero to about 300° C., low coefficient of friction, antisticking, flame resistance and low smoke propagation. Both of the above fluoroolefins are commercially prepared by the high temperature pyrolysis of chlorodifluoromethane which itself is prepared from chloroform. There is a growing concern that chlorinated hydrocarbons pose a threat to the environment, especially the stratospheric ozone layer. Thus, a need now exists to develop fluoromonomer processes which are not chlorine based.

The production of TFE and HFP from precursors without chlorine has been reported. For example, one such process is based on the thermolysis of fluorinated cyclobutanes which can be prepared by electrochemical fluorination. European Patent Application No. 455,399 summarizes the known art describing electrochemical fluorination routes to octafluorocyclobutane and also discloses. . processes for the production of TFE and HFP by the pyrolysis of octafluorocyclobutane.

The use of induction heating to heat packing materials to cause chemical reactions of various types is known. For example, vinylidene fluoride is prepared by the reaction of methane and dichlorodifluoromethane in a reaction tube heated by induction heating and packed with high surface area porous carbon (see U.S Pat. No. 5,110,996, example 5).

SUMMARY OF THE INVENTION

This invention provides a process for producing a perfluoroolefin of the formula $CF(R^1_f)=CF_2$, wherein $R^1_f$ is selected from the group consisting of F and $CF_3$. The process comprises (a) perfluorinating a cyclobutane starting material of the formula

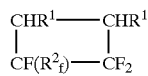

wherein $R^2_f$ is selected from the group consisting of F and $CF_3$ and each $R^1$ is selected from H and $CH_3$ provided that one $R^1$ is H and the other $R^1$ is H when $R^1_f$ is F and is $CH_3$ when $R^1_f$ is $CF_3$) by the Simons electrochemical fluorination process in an electrochemical cell in a solution of anhydrous liquid hydrogen fluoride under temperature and pressure conditions sufficient to replace all hydrogens in the cyclobutane starting material with fluorine; and (b) cracking the perfluorinated cyclobutane. In accordance with this invention, cracking can be accomplished by contacting the perfluorinated cyclobutane provided in (a) with carbon (e.g., graphite or activated carbon) or a conductive metal, which is heated by induction heating to a temperature sufficient to crack said perfluorinated cyclobutane.

DETAILED DESCRIPTION

The partially fluorinated cyclobutane starting materials of this invention can be prepared by thermal cyclodimerization of the olefin $CHR^1=CHR^1$ where $R^1$ is as defined above (i.e., at least one must be H) with the olefin $CF(R^2_f)=CF_2$ where $R^2_f$ is as defined above. This includes the thermal cyclodimerization of ethylene with tetrafluoroethylene (TFE) to produce 1,1,2,2-tetrafluorocyclobutane, the thermal cyclodimerization of ethylene with hexafluoropropylene (HFP) to produce 1-trifluoromethyl-1,2,2-trifluorocyclobutane, the thermal cyclodimerization of propylene with TFE to produce 1,1,2,2-tetrafluoro-3-methylcyclobutane and the thermal cyclodimerization of propylene with HFP to produce 1-trifluoromethyl-1,2,2-trifluoro-3-methylcyclobutane. Typically, the mole ratio of ethylene or propylene to TFE or HFP is in the range of 0.3:1 to 50:1, preferably 5:1 to 20:1. The reactor used can be of any suitable type such as a tube and shell reactor, plug flow or turbulent flow reactor, or a continuous stirred tank reactor as described in EP 455,399. The thermal cycloaddition reaction can be achieved as described in U.S. Pat. No. 3,662,009 and U.S. Pat. No. 3,789,088. Typically, the cyclodimerization can be carried out at a temperature of from about 150° C. to about 600° C., preferably from about 300 to about 450° C. Generally, the reaction pressure will be in the range of about 0.5 to 30 atmospheres, preferably in the range of about 2 to 10 atmospheres. Generally, the residence time is from about 1 second to about 10 minutes, preferably at the preferred temperatures and pressures, from about 1 to 2 minutes.

Of note are processes where in addition to $CF(R^1_f)=CF_2$ product, $CF(R^2_f)=CF_2$ is also produced and used for producing further partially fluorinated cyclobutane starting material by reaction with olefin of the formula $CHR^1=CHR^1$. Of particular note are processes where $R^2_f$ is $CF_3$, and where at least a portion of the hexafluoropropylene produced in (b) is reacted with $CHR^1=CHR^1$ to produce further cyclobutane starting material.

The process of electrolyzing liquid hydrogen fluoride containing an organic chemical which can be fluorinated, at an electrical potential insufficient to generate fluorine gas but sufficient to cause fluorination of the organic chemical is known. This electrochemical fluorination (ECF) is known as the Simons process. This technology has been described in U.S. Pat. No. 2,519,983, which is incorporated herein by reference and which contains a drawing of a Simons cell and its accessories.

The preferred starting materials for the ECF reaction are 1-trifluoromethyl-1,2,2-trifluorocyclobutane (I) and 1-trifluoromethyl-1,2,2-trifluoro-3-methylcyclobutane (II). The perfluorinated cyclobutane product selectivity is greater by about 5% to about 30% when compounds (I) and (II) are used. For both of these partially fluorinated cyclobutanes, the starting perfluoroolefin material for their preparation is hexafluoropropylene rather than tetrafluoroethylene.

The reactor effluent comprising perfluorinated cyclobutanes, hydrogen, hydrogen fluoride and other products, e.g., incompletely fluorinated cyclobutanes, can be separated by conventional techniques such as distillation and decantation.

After separation, the perfluorinated cyclobutanes can be cracked to a product mixture comprising tetrafluoroethylene and/or hexafluoropropylene by passage through an inductively heated reactor such as that described in International Publication No. WO 95/21126. The reactor is packed with a conductive metal, graphite, activated carbon or another carbon. A preferred carbon is a three dimensional matrix carbonaceous material prepared in a similar manner to that disclosed in U.S. Pat. No. 4,978,649.

The temperature within the reaction zone is between about 600° C. to about 1200° C. The residence time in the reactor is between about 30 milliseconds to about 3 seconds, preferably 300 milliseconds.

A diluent gas which is essentially inert under reaction conditions; such as, nitrogen and carbon dioxide, may be used if desired.

The reaction pressure is not critical and may be between about 50 kPa to about 130 kPa.

The hot exit gas leaving the reactor is rapidly cooled by quenching. Any known-art quenching procedures may be used. These include passing the hot exit gas over cold inert surfaces such as the outer surface of a water-cooled body. Alternatively, the hot exit gas may be mixed with a flow of inert cold fluid, e.g., water.

A particular advantage of the present invention is the low amount of perfluoroisobutylene found in the reactor products.

Without further elaboration, it is believed that one skilled in the art can, using the description herein, utilize the present invention to its fullest extent. The following embodiments are to be construed as illustrative, and not as constraining the remainder of the disclosure in any way whatsoever.

EXAMPLES

Legend:

C-318 is perfluorocyclobutane          TFE is $CF_2=CF_2$
HFP is $CF_2=CFCF_3$                   PFIB is $(CF_3)_2C=CF_2$
1318my is $CF_3CF=CFCF_3$              116 is $CF_3CF_3$
c41-10my is heptafluoro(trifluoromethyl)cyclobutane
218 is $CF_3CF_2CF_3$                  31-10mc is $CF_3CF_2CF_2CF_3$
c-456myc is 1-perfluoromethyl-1,2,2-trifluorocyclobutane
c-474stf is 1,1,2,2-tetrafluoro-3-methylcyclobutane General Procedure Fluorinations were done in a Simons electrochemical fluorination cell of the type described in U.S. Pat. No. 2,713,593. Two cells were used. One cell (285 mL capacity) was made of Teflon® poly(tetrafluoroethylene) (Examples 1–4, 6–8); the other cell (150 mL capacity) was fabricated of Hastelloy® nickel alloy (Example 5). The Teflon® cell was equipped with internal cooling/heating coils. The Hastelloy® cell was equipped with external cooling. Both cells were connected to an external condenser to avoid HF losses. Sodium fluoride and gum rubber scrubbers were attached on line to trap any HF or $OF_2$ emitted. A Teflon® poly(tetrafluoroethylene) lined K thermocouple in the reactors was used to monitor the temperature.

The electrode pack consisted of alternating Ni anode and cathode plates, separated by Teflon® poly(tetrafluoroethylene) spacers. Spacing between electrodes was 3 mm. The plates were arranged such that each anode side faced a cathode to ensure even potential distributions at the anode surfaces. Total anode surface area was 185 cm². A $Cu/CuF_2$ reference electrode was used. Electrodes were cleaned by sanding and a dilute nitric acid etch, rinsing, drying and weighing between each run.

Runs were done with continuous addition of starting material for up to 100 hours (continuous batch). Runs were also made circulating the reaction mixture through an external pump. There was no effect on the rates that were run with circulation indicating that the fluorinations were not mass transfer limited.

The potential was applied by an EG&G PAR Model 362 potentiostat connected to a EG&G PAR Model 365 Power Booster. All potentials reported were vs. $Cu/CuF_2$. The amount of charge passed (function of extent of reaction) was monitored by an ESC 640 digital coulometer. Temperature, current, and the potential difference between anodes and cathodes were monitored continuously on an NGI Servogor 120 strip chart recorder.

Products were analyzed on-line using a GC/Mass-Spec equipped with a Krytox® perfluorinated ether capillary column and thermal conductivity and flame ionization detectors. All products are reported in mole percent unless otherwise indicated.

Example 1

Producing TFE

A. Preparation of Perfluorocyclobutane by Electrochemical Fluorination of 1,1,2,2-Tetrafluorocyclobutane To the electrochemical fluorination cell described in the General Procedure was added anhydrous hydrogen fluoride (285 mL), sodium fluoride (1.48 g, 0.124 molar) and 1,1,2,2-tetrafluorocyclobutane (9.12 g, 0.25 molar). The applied voltage was 4.4V vs. $Cu/CuF_2$. The current density ranged between 10 and 20 mA/cm² and averaged 18 mA/cm² throughout the run. The reaction temperature was about 18° C. and the current efficiency was about 85%.

The percent selectivity to octafluorocyclobutane ranged from 13 to 45% during the course of the run. The product amount depended on the initial organic concentration, the higher organic concentration resulted in a lower selectivity. The average selectivity from all products collected in the trap was about 39%.

The percent degradation to mostly partially and fully fluorinated straight chain compounds ranged from 7 to 20 mol percent during the course of the run. The degradation products amount again depended on the initial organic concentration, the higher organic concentration resulted in a higher selectivity to degradation products. The average degradation products from all the materials collected in the trap was about 12.5%.

The balance of the material was incompletely fluorinated starting material.

B. Cracking Perfluorocyclobutane

The octafluorocyclobutane produced in A may be cracked by contact with carbon or a conductive metal which is heated by inductive heating, to produce TFE.

Example 2

Producing TFE

A. Preparation of Perfluorocyclobutane by Electrochemical Fluorination of 1,1,2,2-Tetrafluorocyclobutane To the electrochemical fluorination cell described in the General Procedure was added anhydrous hydrogen fluoride (285 mL), sodium fluoride (0.15 g, 0.024 molar) and 1,1,2,2-tetrafluorocyclobutane (9.12 g, 0.25 molar). The applied voltage was 4.8V vs. $Cu/CuF_2$. The current density ranged between 10 and 40 $mA/cm^2$ and averaged 21 $mA/cm^2$ throughout the run. The reaction temperature was about 18° C. and the current efficiency was about 97%.

The percent selectivity to octafluorocyclobutane ranged from 45 to 66% during the course of the run. The product amount depended on the initial organic concentration, the higher organic concentration resulted in a lower selectivity. The average selectivity from all products collected in the trap was about 62%, corresponding to a yield of 62% with a mass balance of 87%.

The percent degradation to mostly partially and fully fluorinated straight chain compounds ranged from 25 to 45 mol percent during the course of the run. The degradation products amount again depended on the initial organic concentration, the higher organic concentration resulted in a higher selectivity to degradation products. The average degradation products from all the materials collected in the trap was about 29%.

The balance of the material was incompletely fluorinated starting material.

B. Cracking Perfluorocyclobutane

The octafluorocyclobutane produced in A may be cracked by contact with carbon on a conductive metal which is heated by inductive heating, to produce TFE.

Example 3

Producing TFE and HFP

A. Preparation of Heptafluoro(trifluoromethyl)cyclobutane by Electrochemical Fluorination of 1-Perfluoromethyl-1,2,2-Trifluorocyclobutane To the electrochemical fluorination cell described in the General Procedure was added anhydrous hydrogen fluoride (285 mL), sodium fluoride (1.48 g, 0.124 molar) and 1-perfluoromethyl-1,2,2-trifluorocyclobutane (12.69 g, 0.25 molar). The applied voltage was 4.4V vs. $Cu/CuF_2$. The current density ranged between 5 and 15 $mA/cm^2$ and averaged 8 $mA/cm^2$ throughout the run. The reaction temperature was about 18° C. and the current efficiency was about 95%.

The percent selectivity to heptafluoro(trifluoromethyl) cyclobutane ranged from 42 to 77% during the course of the run. The product amount depended on the initial organic concentration, the higher organic concentration resulted in a lower selectivity. The average selectivity from all products collected in the trap was 70%.

The percent degradation to mostly partially and fully fluorinated straight chain compounds ranged from 6 to 40 mol percent during the course of the run. The degradation products amount again depended on the initial organic concentration, the higher organic concentration resulted in a higher selectivity to degradation products. The average degradation products from all the materials collected in the trap was about 12%.

The balance of the material was incompletely fluorinated starting material.

B. Cracking Heptafluoro(trifluoromethyl)cyclobutane

The heptafluoro(trifluoromethyl)cyclobutane produced in A may be cracked by contact with carbon or a conductive metal which is heated by inductive heating to produce TFE and HFP.

Example 4

Producing TFE and HFP

A. Preparation of Heptafluoro(trifluoromethyl)cyclobutane by Electrochemical Fluorination of 1-Perfluoromethyl-1,2,2-Trifluorocyclobutane To the electrochemical fluorination cell described in the General Procedure was added anhydrous hydrogen fluoride (285 mL), sodium fluoride (0.15 g, 0.024 molar) and 1-perfluoromethyl-1,2,2-trifluorocyclobutane (12.69 g, 0.25 molar). The applied voltage was 4.8V vs. $Cu/CuF_2$. The current density ranged between 13 and 25 $mA/cm^2$ and averaged 20 $mA/cm^2$ throughout the run. The reaction temperature was about 18° C. and the current efficiency was about 95%.

The percent selectivity to heptafluoro(trifluoromethyl) cyclobutane ranged from 72 to 90% during the course of the run. The product amount depended on the initial organic concentration, the higher organic concentration resulted in a lower selectivity. The average selectivity from all products collected in the trap was 87%, corresponding to an 87% yield with an 87% mass balance.

The percent degradation to mostly partially and fully fluorinated straight chain compounds ranged from 8 to 18 mol percent during the course of the run. The degradation products amount again depended on the initial organic concentration, the higher organic concentration resulted in a higher selectivity to degradation products. The average degradation products from all the materials collected in the trap was about 10 mol %.

The balance of the material was incompletely fluorinated starting material.

B. Cracking Heptafluoro(trifluoromethyl)cyclobutane

The heptafluoro(trifluoromethyl)cyclobutane produced in A may be cracked by contact with carbon or a conductive metal which is heated by inductive heating to produce TFE and HFP.

Example 5

Producing TFE and HFP

A. Preparation of Heptafluoro(trifluoromethyl)cyclobutane by Electrochemical Fluorination of 1-Perfluoromethyl-1,2,2-Trifluorocyclobutane To the electrochemical fluorination cell described in the General Procedure was added anhydrous hydrogen fluoride (150 mL), sodium fluoride (0.15 g, 0.024 molar) and 1-perfluoromethyl-1,2,2-trifluorocyclobutane (c-456myc), initial concentration was 12.69 g, 0.25 molar). When the concentration of c-356myc dropped to 0.06 molar, a continuous feed of this reactant was begun using a syringe pump. The feed rate was such so as to maintain the concentration of c-356myc at 0.06 molar. The applied voltage was 4.8 V to 5.0 V vs. $Cu/CuF_2$. The current density ranged between 20 and 40 $mA/cm^2$ and averaged 35 $mA/cm^2$ throughout the run. The reaction temperature varied from 35° C. to 52° C. and averaged 45° C. The pressure varied from 20 to 35 psig (239 to 343 kPa) and averaged 28 psig (294 kPa). The current efficiency was about 95%.

The percent selectivity to heptafluoro(trifluoromethyl) cyclobutane was about 82%.

The percent degradation to mostly partially and fully fluorinated straight chain compounds ranged from 8 to 18 mol percent during the course of the run. The degradation products amount again depended on the initial organic concentration, the higher organic concentration resulted in a higher selectivity to degradation products. The average percent degradation products to mostly partially and fully fluorinated straight chain compounds from all the materials collected in the trap was about 15 mol %. The mass balance was 60%.

The balance of the material was incompletely fluorinated starting material.

B. Cracking Heptafluoro(trifluoromethyl)cyclobutane

The heptafluoro(trifluoromethyl)cyclobutane produced in A may be cracked by contact with carbon or a conductive metal which is heated by inductive heating to produce TFE and HFP.

Example 6

Producing TFE and HFP

A. Preparation of Heptafluoro(trifluoromethyl)cyclobutane by Electrochemical Fluorination of 1,1,2,2-Tetrafluoro-3-methylcyclobutane To the electrochemical fluorination cell described in the General Procedure was added anhydrous hydrogen fluoride (285 mL) and 1,1,2,2-tetrafluoro-3-methylcyclobutane (c456myc, 13.68 g, 0.25 molar). The applied voltage was 4.6 V vs. Cu/CuF$_2$. The current density ranged between 1 and 17 mA/cm$^2$ and averaged 9 mA/cm$^2$ throughout the run. The reaction temperature was about 19° C. The current efficiency was about 75%.

The percent selectivity to heptafluoro(trifluoromethyl) cyclobutane was about 20% and the percent selectivity to perfluorocyclopentane was about 57%.

The percent degradation to mostly octafluorocyclobutane, tetrafluoromethane and small amounts of straight chain compounds ranged from 7 to 10 mol percent during the course of the run. The degradation products amount again depended on the initial organic concentration, the higher organic concentration resulted in a higher selectivity to degradation products.

The balance of the material was incompletely fluorinated starting material.

B. Cracking Heptafluoro(trifluoromethyl)cyclobutane

The heptafluoro(trifluoromethyl)cyclobutane produced in A may be cracked by contact with carbon or a conductive metal which is heated by inductive heating to produce TFE and HFP.

Example 7

Producing TFE and HFP

A. Preparation of Heptafluoro(trifluoromethyl)cyclobutane by Electrochemical Fluorination of 1,1,2,2-Tetrafluoro-3-methylcyclobutane To the electrochemical fluorination cell described in the General Procedure was added anhydrous hydrogen fluoride (285 mL), sodium fluoride (1.48 g, 0.124 molar) and 1,1,2,2-tetrafluoro-3-methylcyclobutane (c456myc, 13.68 g, 0.25 molar). The applied voltage was 4.6 V vs. Cu/CuF$_2$. The current density ranged between 13 and 20 mA/cm$^2$ and averaged 15 mA/cm$^2$ throughout the run. The reaction temperature was about 17° C. The current efficiency was about 95%.

The percent selectivity to heptafluoro(trifluoromethyl) cyclobutane was from between about 15% to about 30% during the course of the run. The percent selectivity to perfluorocyclopentane was from between about 30% to about 50% during the course of the run.

The percent degradation to mostly octafluorocyclobutane, tetrafluoromethane and small amounts of straight chain compounds ranged from 5 to 20 mol percent during the course of the run. The degradation products amount again depended on the initial organic concentration, the higher organic concentration resulted in a higher selectivity to degradation products.

The balance of the material was incompletely fluorinated starting material.

B. Cracking Heptafluoro(trifluoromethyl)cyclobutane

The heptafluoro(trifluoromethyl)cyclobutane produced in A may be cracked by contact with carbon or a conductive metal which is heated by inductive heating to produce TFE and HFP.

Example 8

Producing TFE and HFP

A. Preparation of Heptafluoro(trifluoromethyl)cyclobutane by Electrochemical Fluorination of 1,1,2,2-Tetrafluoro-3-methylcyclobutane To the electrochemical fluorination cell described in the General Procedure was added anhydrous hydrogen fluoride (285 mL), sodium fluoride (11.94 g, 1.0 molar) and 1,1,2,2-tetrafluoro-3-methylcyclobutane (c-474stf, (13.68 g, 0.25 molar)). The applied voltage was 4.6 V vs. Cu/CuF$_2$. The current density ranged between 1 and 25 mA/cm$^2$ and averaged 15 mA/cm$^2$ throughout the run. The reaction temperature was about 20° C. The current efficiency was about 95%.

The percent selectivity to heptafluoro(trifluoromethyl) cyclobutane was from between about 35% to about 42% during the course of the run. The percent selectivity to perfluorocyclopentane was from between about 15% to about 22% during the course of the run.

The percent degradation to mostly octafluorocyclobutane, tetrafluoromethane and small amounts of straight chain compounds ranged from 10 to 30 mol percent during the course of the run. The degradation products amount again depended on the initial organic concentration, the higher organic concentration resulted in a higher selectivity to degradation products.

The balance of the material was incompletely fluorinated starting material.

B. Cracking Heptafluoro(trifluoromethyl)cyclobutane

The heptafluoro(trifluoromethyl)cyclobutane produced in A may be cracked by contact with carbon or a conductive metal which is heated by inductive heating to produce TFE and HFP.

Example 9

Preparation of Tetrafluoroethylene by Thermolysis of Perfluorocyclobutane

The apparatus used for induction heating in this invention consisted of a 12 mm diameter quartz tube, placed inside a copper solenoid which generated the necessary alternating magnetic field. The coil was comprised of 8 turns over a height of 6 cm. A separate coupling coil, which couples the energy into the main coil was located below the main coil and had 2 turns over a height of 1.5 cm. A capacitor was connected in parallel with the main coil and resonated the coil at the frequency of interest. Flowing water was passed through the coils and around the capacitor for cooling. The power was generated and amplified by commercially available equipment and was transferred to the reactor through 50 ohm cable. The carbon catalyst was located inside of the quartz tube. The perfluorinated cyclobutanes were fed through a port and the reaction products were removed through a different port. The induction heating apparatus was housed in an aluminum enclosure. The apparatus essentially corresponded to the diagram of an apparatus disclosed in WO 95/21126.

Carbon (0.5 g) which consisted of three dimensional matrix carbonaceous material prepared in a similar manner to that disclosed in U.S. Pat. No. 4,978,649 was placed in a ¼" (6.4 mm) O.D. quartz tube reactor inside the induction heating coils. Perfluorocyclobutane (12 sccm, (2.0×10$^{-7}$ m$^3$/s)) and nitrogen (188 sccm, (3.1×10$^{-6}$ m$^3$/s)) were passed over the carbon. The contact time was 0.3 seconds, equivalent to a gas hourly space velocity of 10993, for all the runs. Results in mole percent at different power outputs are shown in Table 1.

TABLE 1

| Watts | % C-318 Conv. | % Sel. TFE | % Sel. HFP | % Sel. PFIB | % Sel. 1318my | % Sel. Others |
|---|---|---|---|---|---|---|
| 40 | 58.2 | 95.4 | 2.1 | 0.3 | 0.2 | 2.0 |
| 45 | 79.0 | 93.0 | 4.2 | 0.5 | 0.3 | 2.0 |
| 50 | 95.8 | 85.9 | 10.0 | 0.9 | 0.3 | 2.9 |

Example 10

Preparation of Tetrafluoroethylene and Hexafluoropropylene by Thermolysis of Heptafluoro(trifluoromethyl)cyclobutane The apparatus used and the procedure followed was the same as that used in Example 9. Heptafluoro (trifluoromethyl)cyclobutane (12 sccm, (2.0×10$^{-7}$ m$^3$/s)) and nitrogen (188 sccm, (3.1×10$^{-6}$ m$^3$/s)) were passed over the carbon. The contact time was 0.3 seconds, equivalent to a gas hourly space velocity of 10993, for all the runs. Results in area % at 40 watts are shown in Table 2.

TABLE 2

| Run No. | % Sel. c-41-10my | % Sel. TFE | % Sel. HFP | % Sel. PFIB | % Sel. 116 | % Sel. 218 | % Sel. 31-10mc | % Sel. Others |
|---|---|---|---|---|---|---|---|---|
| 1 | 1.3 | 21.5 | 64.2 | 2.9 | 0.4 | 1.7 | 1.6 | 7.3 |
| 2 | 1.4 | 25.8 | 61.0 | 1.5 | 1.1 | 1.3 | 0.8 | 7.1 |

What is claimed is:

1. A process for producing a perfluoroolefin of the formula $CF(R^1_f)=CF_2$, wherein $R^1_f$ is selected from the group consisting of F and $CF_3$, comprising:

(a) perfluorinating a cyclobutane starting material of the formula

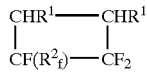

wherein $R^2_f$ is selected from the group consisting of F and $CF_3$ and each $R^1$ is selected from H and $CH_3$, provided that one $R^1$ is H and the other $R^1$ is H when $R^1_f$ is F and is $CH_3$ when $R^1_f$ is $CF_3$, by the Simons electrochemical fluorination process in an electrochemical cell in a solution of anhydrous liquid hydrogen fluoride under temperature and pressure conditions sufficient to replace all hydrogens in the cyclobutane starting material with fluorine; and (b) contacting the perfluorinated cyclobutane produced in (a) with carbon or a conductive metal, which is heated by induction heating to a temperature sufficient to crack said perfluorinated cyclobutane.

2. The process of claim 1 wherein in (a) 1,1,2,2-tetrafluorocyclobutane is perfluorinated.

3. The process of claim 2 wherein said 1,1,2,2-tetrafluorocyclobutane is produced by thermal cyclodimerization of ethylene with tetrafluoroethylene.

4. The process of claim 1 wherein in (a) 1-trifluoromethyl-1,2,2-trifluorocyclobutane is perfluorinated.

5. The process of claim 4 wherein said 1-trifluoromethyl-1,2,2,-trifluorocyclobutane is produced by thermal cyclodimerization of ethylene with hexafluoropropylene.

6. The process of claim 1 wherein in (a) 1,1,2,2-tetrafluoro-3-methylcyclobutane is perfluorinated.

7. The process of claim 6 wherein said 1,1,2,2-tetrafluoro-3-methylcyclobutane is produced by thermal cyclodimerization of propylene with tetrafluoroethylene.

8. The process of claim 1 wherein in (a) 1-trifluoromethyl-1,2,2-trifluoro-3-methylcyclobutane is perfluorinated.

9. The process of claim 8 wherein said 1-trifluoromethyl-1,2,2-trifluoro-3-methylcyclobutane is produced by thermal cyclodimerization of propylene with hexafluoropropylene.

10. The process of claim 1 wherein $CF(R^2_f)=CF_2$ is produced in addition to $CF(R^1_f)=CF_2$, wherein $R^2_f$ is $CF_3$, and wherein at least a portion of the hexafluoropropylene produced in (b) is reacted with olefin of the formula $CHR^1=CHR^1$ to produce further cyclobutane starting material.

11. A process for producing a perfluoroolefin of the formula $CF(R^1_f)=CF_2$ wherein $R^1_f$ is F, comprising:

(a) perfluorinating a cyclobutane starting material of the formula

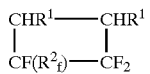

wherein $R^2_f$ is $CF_3$ and each $R^1$ is H, by the Simons electrochemical fluorination process in an electrochemical cell in a solution of anhydrous liquid hydrogen fluoride under temperature and pressure conditions sufficient to replace all hydrogens in the cyclobutane starting material with fluorine;

(b) cracking the perfluorinated cyclobutane produced in (a) to produce said $CF(R^1_f)=CF_2$ product and a perfluoroolefin of the formula $CF(R^2_f)=CF_2$; and (c) reacting at least a portion of the hexafluoropropylene produced in (b) with $CH_2=CH_2$ to produce further cyclobutane starting material.

12. The process of claim 11 wherein the perfluorinated cyclobutane produced in (a) is contacted in (b) with carbon or a conductive metal, which is heated by induction heating to a temperature sufficient to crack said perfluorinated cyclobutane.

13. A process for producing a perfluoroolefin of the formula $CF(R^1_f)=CF_2$ wherein $R^1_f$ is $CF_3$, comprising:

(a) perfluorinating a cyclobutane starting material of the formula

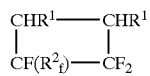

wherein $R^2_f$ is $CF_3$, one $R^1$ is H and the other $R^1$ is $CH_3$, by the Simons electrochemical fluorination process in an electrochemical cell in a solution of anhydrous liquid hydrogen fluoride under temperature and pressure conditions sufficient to replace all hydrogens in the cyclobutane starting material with fluorine;

(b) cracking the perfluorinated cyclobutane produced in (a) to produce said $CF(R^1_f)=CF_2$ product and a perfluoroolefin of the formula $CF(R^2_f)=CF_2$; and (c) reacting at least a portion of the hexafluoropropylene produced in (b) with $CH_2=CHCH_3$ to produce further cyclobutane starting material.

14. The process of claim 13 wherein the perfluorinated cyclobutane produced in (a) is contacted in (b) with carbon or a conductive metal, which is heated by induction heating to a temperature sufficient to crack said perfluorinated cyclobutane.

15. The process of claim 13 wherein in (a) 1-trifluoromethyl-1,2,2-trifluoro-3-methylcyclobutane is perfluorinated.

16. The process of claim 15 wherein the perfluorinated cyclobutane produced in (a) is contacted in (b) with carbon or a conductive metal, which is heated by induction heating to a temperature sufficient to crack said perfluorinated cyclobutane.

* * * * *